(12) United States Patent
Jung et al.

(10) Patent No.: US 11,759,164 B2
(45) Date of Patent: Sep. 19, 2023

(54) X-RAY DETECTOR INTEGRAL WITH AUTOMATIC EXPOSURE CONTROL DEVICE

(71) Applicant: LG ELECTRONICS INC., Seoul (KR)

(72) Inventors: Youngjun Jung, Seoul (KR); Seungchan Baek, Seoul (KR); Taehyung Kim, Seoul (KR); Sangjun Park, Seoul (KR); Mikiko Ito, Seoul (KR); Hyoungjoon Jo, Seoul (KR)

(73) Assignee: LG ELECTRONICS INC, Seoul (KR)

( * ) Notice: Subject to any disclaimer, the term of this patent is extended or adjusted under 35 U.S.C. 154(b) by 0 days.

(21) Appl. No.: 17/542,095

(22) Filed: Dec. 3, 2021

(65) Prior Publication Data

US 2022/0386982 A1    Dec. 8, 2022

(30) Foreign Application Priority Data

Jun. 4, 2021  (WO) ................ PCT/KR2021/007000

(51) Int. Cl.
*A61B 6/00*    (2006.01)
*G01T 1/202*   (2006.01)
*G01T 1/20*    (2006.01)
*G01T 1/24*    (2006.01)

(52) U.S. Cl.
CPC ............ *A61B 6/542* (2013.01); *A61B 6/4208* (2013.01); *G01T 1/2018* (2013.01); *G01T 1/2023* (2013.01); *G01T 1/24* (2013.01)

(58) Field of Classification Search
CPC ..... A61B 6/542; A61B 6/4208; G01T 1/2018; G01T 1/2023; G01T 1/24
See application file for complete search history.

(56) References Cited

U.S. PATENT DOCUMENTS

| | | | | |
|---|---|---|---|---|
| 5,751,783 | A * | 5/1998 | Granfors | ................ A61B 6/542 378/97 |
| 6,192,105 | B1 | 2/2001 | Hunter et al. | |
| 6,404,851 | B1 * | 6/2002 | Possin | .................. G01T 1/2928 348/E3.019 |
| 2008/0112535 | A1 * | 5/2008 | Wojcik | .................... G01T 1/244 250/366 |

(Continued)

FOREIGN PATENT DOCUMENTS

| | | | | |
|---|---|---|---|---|
| CN | 108567437 | A * | 9/2018 | ........... A61B 6/4208 |
| JP | 2014-122903 | A | 7/2014 | |

(Continued)

OTHER PUBLICATIONS

Translation of CN-108567437A (Year: 2017).*

*Primary Examiner* — David P Porta
*Assistant Examiner* — Mamadou Faye
(74) *Attorney, Agent, or Firm* — Birch, Stewart, Kolasch & Birch, LLP

(57) ABSTRACT

An X-ray detector integral with an automatic exposure control (AEC) device can include an X-ray detection part configured to detect X-rays irradiated from an X-ray source and generate X-ray image data; and an automatic exposure detection board located below the X-ray detection part and configured to generate an X-ray sensing signal for automatic exposure control based on residual X-rays which have passed by or through the X-ray detection part.

13 Claims, 8 Drawing Sheets

(56) References Cited

U.S. PATENT DOCUMENTS

| | | | |
|---|---|---|---|
| 2011/0164723 A1 | 7/2011 | Park et al. | |
| 2013/0058454 A1* | 3/2013 | Kuwabara | A61B 6/548 378/62 |
| 2013/0058457 A1* | 3/2013 | Kuwabara | A61B 6/548 378/97 |
| 2013/0126742 A1* | 5/2013 | Hayun | G01T 1/2018 250/366 |
| 2013/0148784 A1* | 6/2013 | Tajima | A61B 6/4283 378/62 |
| 2014/0312237 A1* | 10/2014 | Hosoi | G21K 4/00 250/363.01 |
| 2014/0348299 A1 | 11/2014 | Sung et al. | |
| 2015/0164459 A1* | 6/2015 | Ito | A61B 6/4233 378/97 |
| 2017/0281103 A1 | 10/2017 | Han et al. | |
| 2018/0353150 A1* | 12/2018 | Takeshima | A61B 6/56 |
| 2020/0209414 A1* | 7/2020 | Birowosuto | G01T 1/20 |
| 2021/0003722 A1* | 1/2021 | Kato | G01T 1/20188 |

FOREIGN PATENT DOCUMENTS

| | | |
|---|---|---|
| KR | 10-2011-0080363 A | 7/2011 |
| KR | 10-1377115 B1 | 6/2014 |
| KR | 10-1835089 B1 | 3/2018 |

\* cited by examiner

X-RAY DETECTOR INTEGRAL WITH AUTOMATIC EXPOSURE CONTROL DEVICE

CROSS-REFERENCE TO RELATED APPLICATIONS

The present application claims the benefit of priority under 35 U.S.C. § 119 and 35 U.S.C. § 365 to PCT Application No. PCT/KR2021/007000 filed on Jun. 4, 2021, which is hereby incorporated by reference in its entirety.

BACKGROUND

The present disclosure relates to an X-ray detector for an automatic exposure control (AEC) device and, more particularly, to an X-ray detector integral with an AEC device, which detects X-rays irradiated to a subject to generate X-ray image data and generates an X-ray sensing signal for automatic exposure control.

When taking X-rays, automatic exposure control (AEC) is used to adjust the amount of irradiated X-rays according to the gender, age and body part of a subject (e.g., a patient).

In a conventional X-ray imaging system, irradiated X-rays are input to an automatic exposure control device and then are input to an X-ray detector. Accordingly, a sensor of the automatic exposure control device may be expressed as an afterimage in the X-ray image.

In addition, since the automatic exposure control device and the X-ray detector are separately present, there is a need for an additional device for constantly maintaining the positions of the automatic exposure control device and the X-ray detector when taking X-rays.

Accordingly, there is a need for integrating the automatic exposure control device with the X-ray detector.

SUMMARY

An object of the present disclosure is to provide an X-ray detector integral with an AEC device, which prevents a sensor of the AEC device from appearing as an afterimage in an X-ray image.

An object of the present disclosure is to provide an X-ray detector integral with an AEC device, which does not require an additional device for constantly maintaining positions of the AEC device and the X-ray detector.

An object of the present disclosure is to provide an X-ray detector integral with an AEC device, which enhances portability by transmitting X-ray image data and an X-ray sensing signal for AEC to an external device through wireless communication.

An X-ray detector integral with an automatic exposure control (AEC) device according to an embodiment of the present disclosure includes an X-ray detection unit configured to detect incident X-rays irradiated from an X-ray source and to generate X-ray image data and an automatic exposure detection board located below the X-ray detection unit and configured to generate an X-ray sensing signal for automatic exposure control based on residual X-rays which have passed through the X-ray detection unit.

DETAILED DESCRIPTION OF THE EMBODIMENTS

Figure 1:
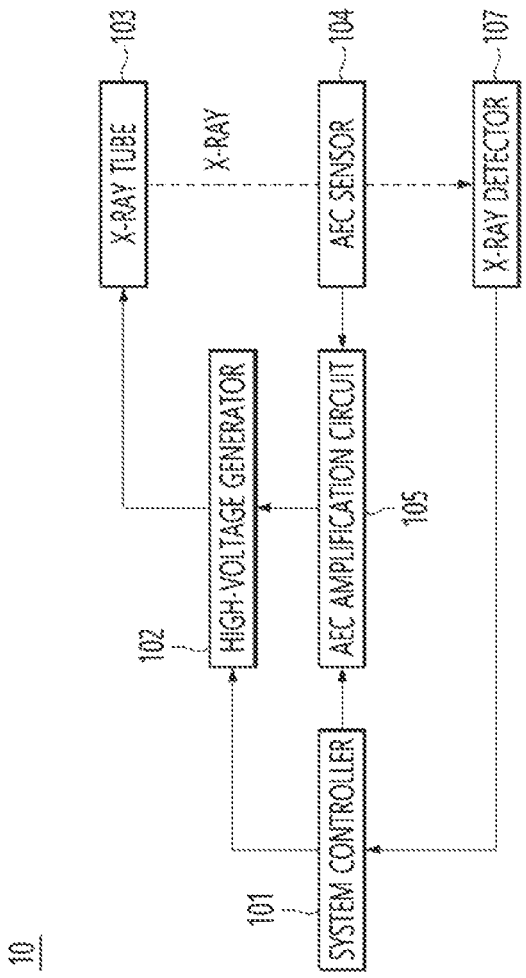
FIG. 1 is a view illustrating a conventional X-ray imaging system.

Hereinafter, embodiments of the present disclosure are described in more detail with reference to accompanying drawings and regardless of the drawings symbols, same or similar components are assigned with the same reference numerals and thus overlapping descriptions for those are omitted. The suffixes "module" and "unit" for components used in the description below are assigned or mixed in consideration of easiness in writing the specification and do not have distinctive meanings or roles by themselves. In the following description, detailed descriptions of well-known functions or constructions will be omitted since they would obscure the invention in unnecessary detail. Additionally, the accompanying drawings are used to help easily understanding embodiments disclosed herein but the technical idea of the present disclosure is not limited thereto. It should be understood that all of variations, equivalents or substitutes contained in the concept and technical scope of the present disclosure are also included.

It will be understood that the terms "first" and "second" are used herein to describe various components but these components should not be limited by these terms. These terms are used only to distinguish one component from other components.

In this disclosure below, when one part (or element, device, etc.) is referred to as being 'connected' to another part (or element, device, etc.), it should be understood that the former can be 'directly connected' to the latter, or 'electrically connected' to the latter via an intervening part (or element, device, etc.). It will be further understood that when one component is referred to as being 'directly connected' or 'directly linked' to another component, it means that no intervening component is present.

FIG. 1 is a view illustrating a conventional X-ray imaging system.

The conventional X-ray imaging system 10 may include a system controller 101, a high-voltage generator 102, an X-ray tube 103, an automatic exposure control (ACE) device 104 and an X-ray detector 106. Meanwhile, the AEC device 104 may include an AEC sensor 104 and an AEC amplification circuit 105. The AEC device 104 may prevent excessive exposure to a subject.

Meanwhile, the system controller 101, the high-voltage generator 102, the X-ray tube 130, the AEC sensor 104 and the AEC amplification circuit 105 transmit and receive data through wired communication. In addition, the system controller 101 and the X-ray detector 106 may transmit and receive data through wired or wireless communication.

The system controller 101 may set X-ray irradiation conditions. The system controller 101 may set X-ray irradiation conditions including a tube voltage, tube current and an X-ray irradiation time. The system controller 101 may transmit the set X-ray irradiation conditions to the high-voltage generator 102.

In addition, the system controller 101 may select an AEC sensing area of the AEC device 104 and transmit information on the selected AEC sensing area to the AEC device 104.

The high-voltage generator 102 may apply a tube voltage and tube current to the X-ray tube 103 during the set irradiation time based on the set X-ray irradiation conditions.

The tube voltage and tube current may be applied to the X-ray tube 103 by the high-voltage generator 102, thereby irradiating X-rays toward the X-ray detector 106.

Current may be generated when X-rays are input to The AEC sensor 104, and the AEC sensor may transmit an X-ray sensing signal corresponding to the generated current to the AEC amplification circuit 106.

The AEC amplification circuit 106 may amplify the X-ray sensing signal and transmit the amplified X-ray sensing signal to the high-voltage generator 102.

The high-voltage generator 102 may determine whether the dose of currently incident X-rays exceeds a threshold dose based on the amplified X-ray sensing signal. When the dose of X-rays exceeds the threshold dose, the tube voltage and tube current applied to the X-ray tube 103 may be stopped.

The X-ray detector 107 may generate an electrical signal corresponding to the dose of transmitted X-rays and generate X-ray image data. The X-ray detector 107 may transmit the X-ray image data to the system controller 101.

Meanwhile, in the conventional X-ray imaging system 10, X-rays are input to the X-ray detector 107 after passing through the AEC sensor 104. Accordingly, the AEC sensor 104 may be expressed as an afterimage in the X-ray image. In addition, an additional device (e.g., a bucky) for constantly maintaining the positions of the AEC device 104 and the X-ray detector 107 is required. In addition, since the X-ray sensing signal of the AEC device 104 is transmitted to the system controller 101 or the high-voltage generator 102 using wired communication, a wired cable is separately required and application to a portable X-ray imaging system is difficult.

Accordingly, it is necessary to integrate the AEC device 104 with the X-ray detector 107.

Figure 2:
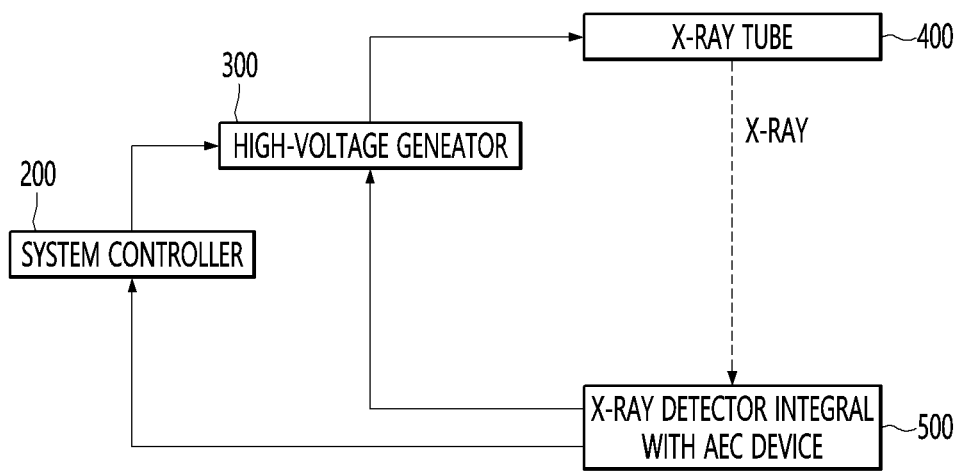
FIG. 2 is a view illustrating an X-ray imaging system according to an embodiment of the present disclosure.

FIG. 2 is a view illustrating an X-ray imaging system according to an embodiment of the present disclosure.

The X-ray imaging system 20 can include a system controller 200, a high-voltage generator 300, an X-ray tube 400 and an X-ray director 500 integral with an AEC device. The X-ray detector 500 integral with the AEC device can include an AEC sensor and an AEC amplification circuit.

The system controller 200 can set X-ray irradiation conditions. The system controller 200 can set X-ray irradiation conditions including a tube voltage, tube current and an X-ray irradiation time. The system controller 200 can transmit the set X-ray irradiation conditions to the high-voltage generator 300.

In addition, the system controller 200 can select an AEC sensing area and transmit information on the selected AEC sensing area to the X-ray detector 500 integral with the AEC device.

The high-voltage generator 300 can apply a tube voltage and tube current to the X-ray tube 400 based on the set X-ray irradiation conditions during the set irradiation time.

The tube voltage and tube current can be applied to the X-ray tube 400 by the high-voltage generator 300, thereby irradiating X-rays toward the X-ray detector 500 integral with the AEC device.

The X-ray detector 500 integral with the AEC device can generate an X-ray sensing signal corresponding to current generated when X-rays are input, amplify the generated X-ray sensing signal, and transmit the amplified X-ray sensing signal to the high-voltage generator 300. The X-ray sensing signal can be a signal for monitoring the amount of irradiated X-rays.

The high-voltage generator 300 can determine whether the dose of currently incident X-rays exceeds a threshold dose based on the amplified X-ray sensing signal. When the dose of X-rays exceeds the threshold dose, the tube voltage and tube current applied to the X-ray tube 400 can be stopped.

The X-ray detector 500 integral with the AEC device can generate an electrical signal corresponding to the dose of transmitted X-rays and generate X-ray image data. The X-ray detector 500 integral with the AEC device can transmit the X-ray image data to the system controller 200.

Meanwhile, the system controller 200, the high-voltage generator 300 and the X-ray tube 400 can transmit and receive data through wired communication. In addition, the system controller 200, the high-voltage generator 300 and the X-ray detector 500 integral with the AEC device can transmit and receive data through wired or wireless communication.

Meanwhile, the X-ray imaging system 20 can solve a problem that the AEC sensor are expressed as an afterimage in the X-ray image, unlike the conventional X-ray imaging system. In addition, an additional device for constantly maintaining the position of the AEC device and the X-ray detector is not necessary. In addition, the system controller 200, the high-voltage generator 300 and the X-ray detector 500 integral with the AEC device can transmit and receive data through wireless communication, thereby constructing a movable X-ray imaging system.

Figure 3:
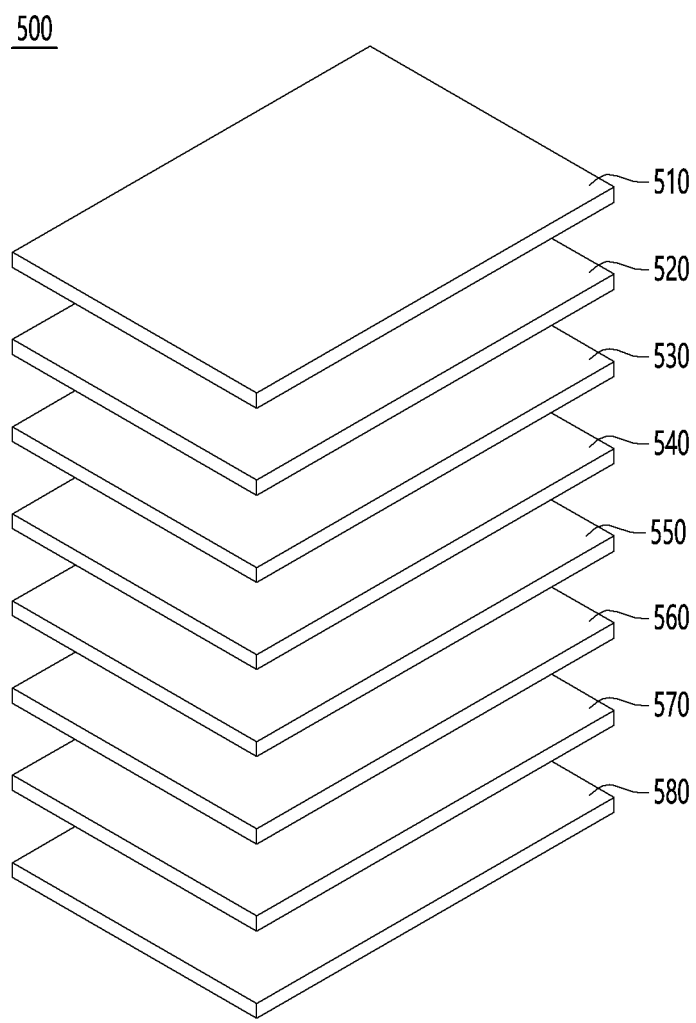
FIG. 3 is a view illustrating a stacked structure of an X-ray detector integral with an AEC device according to an embodiment of the present disclosure.

FIG. 3 is a view illustrating a stacked structure of an X-ray detector integral with an AEC device according to an embodiment of the present disclosure.

Referring to FIG. 3, the X-ray detector 500 integral with the AEC device can include an upper frame 510, an X-ray detection unit 520 (e.g., an X-ray detection part including one or more sensors), an electromagnetic wave absorption sheet 530, a scattering prevention sheet 540, a driving circuit fixing plate 550, an automatic exposure detector (AED) 560, a battery unit 570 and a lower frame 580.

The upper frame 510 can protect the internal components of the X-ray detector 500 integral with the AEC device and absorb external impact.

Figure 4:
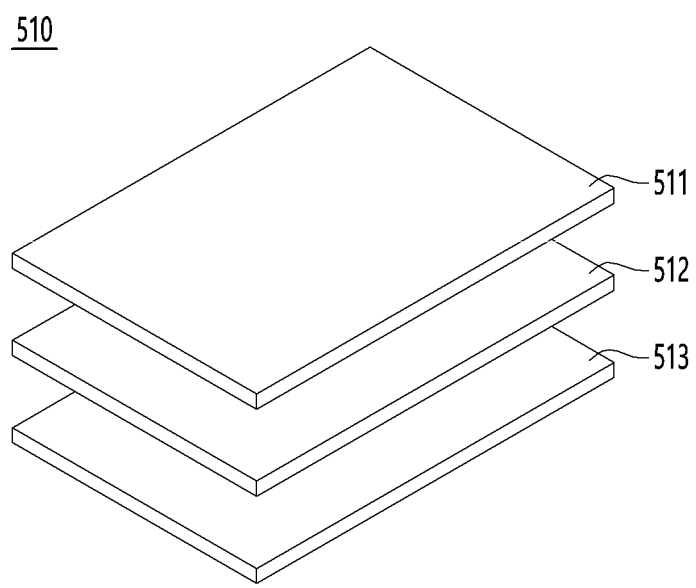
FIG. 4 is a view illustrating a stacked structure of an upper frame according to an embodiment of the present disclosure.

FIG. 4 is a view illustrating a stacked structure of an upper frame according to an embodiment of the present disclosure.

Referring to FIG. 4, the upper frame 510 can include a decorative sheet 511, a plate 512 and a pad 513. The decorative sheet 511 can include a pattern capable of adjusting a center to which the X-rays are irradiated. The decorative sheet 511 can be provided on the plate 512. In addition, the plate 512 can be a carbon fiber reinforced plastic (CFRP) plate but is not limited thereto and can be a melamine or polycarbonate plate. The plate 512 can protect the X-ray detection unit 520 placed therebelow. In addition, the pad 513 can be a high-density polyethylene (HDPE) pad. The pad 513 can reduce impact to protect the X-ray detection unit 520.

Meanwhile, the X-ray detection unit 520 can detect X-rays using a direct conversion method or an indirect conversion method. The X-ray detection unit 520 can generate X-ray image data for a subject based on the detected X-rays.

The direct conversion method refers to a method of directly converting X-ray photons into an electrical signal through a photoconductor material.

Figure 5:
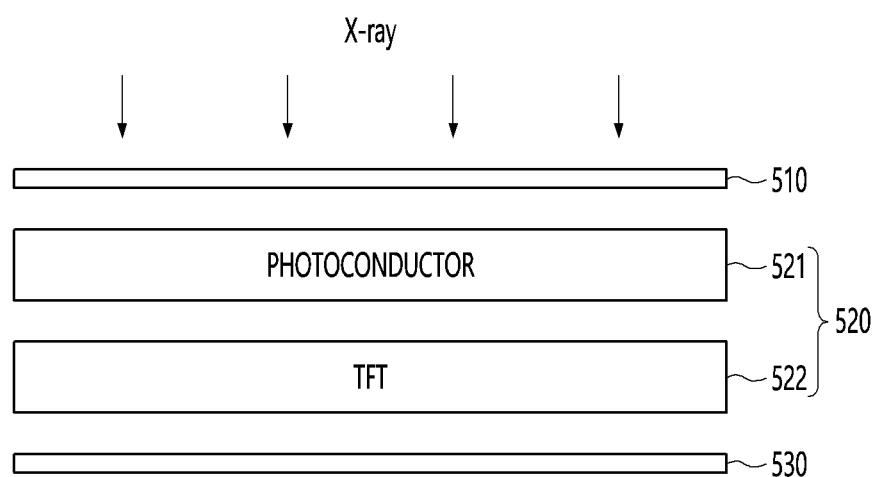
FIG. 5 is a view illustrating a direct-type X-ray detection unit according to an embodiment of the present disclosure.

FIG. 5 is a view illustrating a direct-type X-ray detection unit according to an embodiment of the present disclosure.

Referring to FIG. 5, the direct-type X-ray detection unit 520 can include a photoconductor 521 and a thin-film transistor (TFT) 522. The photoconductor 521 generates an electron-hole pair when absorbing X-rays. Meanwhile, the photoconductor 521 can include at least one of amorphous selenium, perovskite, Cadmium Telluride (CdTe) or cadmium zinc telluride (CdZnTe), and the TFT 522 can detect the dose of incident X-rays based on the generated electron-hole pair as an electrical signal.

Meanwhile, a direct conversion method refers to a method of detecting X-rays by converting incident X-rays into visible rays and converting the visible rays into an electrical signal.

Figure 6:
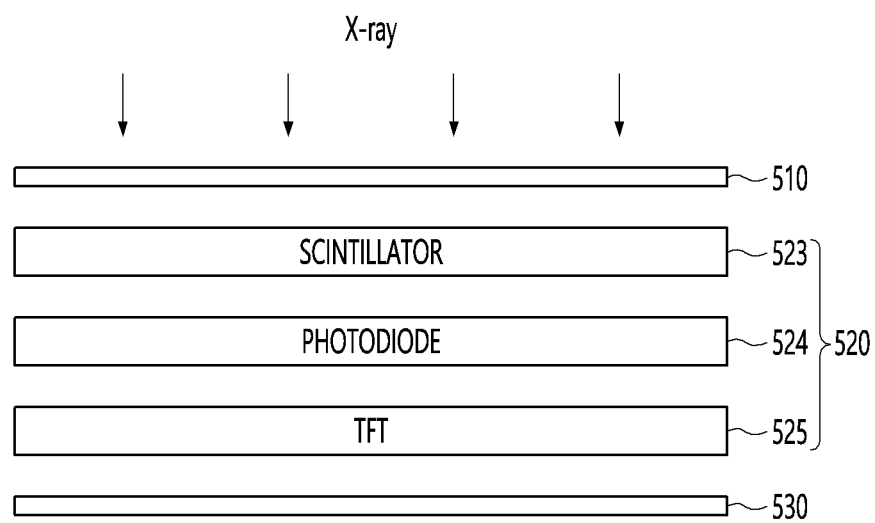
FIG. 6 is a view illustrating an indirect-type X-ray detection unit according to an embodiment of the present disclosure.

FIG. 6 is a view illustrating an indirect-type X-ray detection unit according to an embodiment of the present disclosure.

Referring to FIG. 6, the indirect-type X-ray detection unit 520 can include a scintillator 523, a photodiode 524 and a thin-film transistor (TFT) 525. The scintillator 523 can convert incident X-rays into visible rays. The scintillator 523 can include at least one of gadolinium oxysulfide (GoS), cesium iodide (CsI) or perovskite.

Perovskite can include a perovskite compound represented by Formula 1 below.

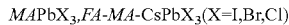

$$MAPbX_3, FA\text{-}MA\text{-}CsPbX_3(X=I,Br,Cl) \quad \text{[Formula 1]}$$

The photodiode 524 can detect visible rays converted by the scintillator 523. The photodiode 524 can convert the visible rays into the electrical signal. The TFT 525 can output the electrical signal converted by the photodiode 524.

Referring to FIG. 3 again, the electromagnetic wave absorption sheet 530 can be located below the X-ray detection unit 520. The electromagnetic wave absorption sheet 530 can protect the TFTs 522 and 525 of the X-ray detection unit 520 from influence of an external magnetic field.

Meanwhile, the scattering prevention sheet 540 can include a sheet for preventing backscattering of X-rays. The scattering prevention sheet 540 can include a PE/PB sheet.

Meanwhile, the driving circuit fixing plate 550 can fix the driving circuit of the X-ray detector 500 integral with the AEC device. The driving circuit can include a photodiode for detecting X-rays, a communication unit (e.g., a transmitter or a transceiver) for transmitting the detected X-ray sensing signal to an external device (e.g., the system controller 200 or the high-voltage generator 300), and a processor for controlling them.

Meanwhile, the automatic exposure detection (AED) board 560 performs an automatic exposure control (AEC) function and prevents excessive exposure to a subject. The AED board 560 can detect residual X-rays after passing through the X-ray detection unit 520. For example, the dose of X-rays input to the AED board 560 can be about 2% of the dose of X-rays emitted from the X-ray tube 400.

Figure 7:
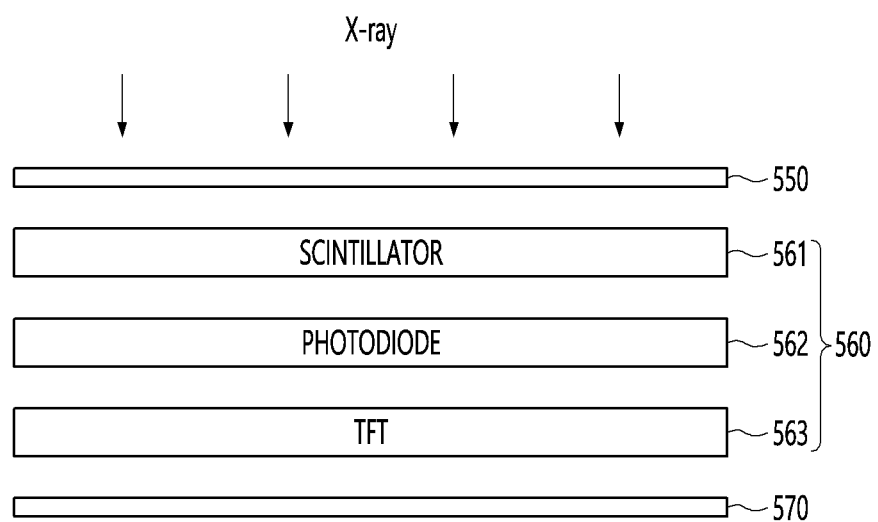
FIG. 7 is a view illustrating an automatic exposure detection board according to an embodiment of the present disclosure.

FIG. 7 is a view illustrating an automatic exposure detection board according to an embodiment of the present disclosure.

The AED board 560 can include a scintillator 561, a photodiode 562 and a TFT 563.

The scintillator 561 can convert incident X-rays into visible rays. The scintillator 561 can include at least one of gadolinium oxysulfide (GoS), cesium iodide (CsI) or perovskite.

Perovskite can include a perovskite compound represented by Formula 1 below.

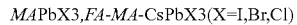

$$MAPbX3, FA\text{-}MA\text{-}CsPbX3(X=I,Br,Cl) \quad \text{[Formula 1]}$$

The photodiode 562 can detect visible rays converted by the scintillator 561. The photodiode 562 can convert the visible rays into the electrical signal. The TFT 563 can include an amplification circuit for amplifying the electrical signal converted by the photodiode 562, and output the amplified electrical signal.

Figure 8:
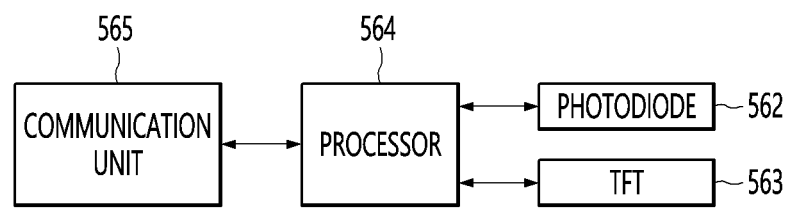
FIG. 8 is a block diagram illustrating an automatic exposure detection board according to an embodiment of the present disclosure.

FIG. 8 is a block diagram illustrating an automatic exposure detection board according to an embodiment of the present disclosure.

The AED board 560 can include a processor 564 for obtaining an amplified electrical signal as an X-ray sensing signal. In addition, the processor 564 can transmit the obtained X-ray sensing signal to the system controller 200 or the high-voltage generator 300 through the communication unit 565.

The processor 564 can determine at least one executable operation of the AED board 560 and control the components of the AED board 560 to perform the determined operation.

Communication technology used by the communication unit 565 can include Global System for Mobile communication (GSM), Code Division Multi Access (CDMA), Long Term Evolution (LTE), 5G, Wireless LAN (WLAN), Wireless-Fidelity (Wi-Fi), Bluetooth™, Radio Frequency Identification (RFID), Infrared Data Association (IrDA), ZigBee, Near Field Communication (NFC), etc.

Referring to FIG. 3 again, the battery unit 570 can include a battery for supplying power necessary for operation of the X-ray detector 500 integral with the AEC device.

In addition, the lower frame 580 can protect the internal components of the X-ray detector 500 integral with the AEC device and absorb external impact.

According to an embodiment of the present disclosure, it is possible to provide an X-ray detector integral with an AEC device, which prevents a sensor of the AEC device from appearing as an afterimage in an X-ray image.

According to an embodiment of the present disclosure, it is possible to provide an X-ray detector integral with an AEC device, which does not require an additional device for constantly maintaining positions of the AEC device and the X-ray detector.

According to an embodiment of the present disclosure, it is possible to provide an X-ray detector integral with an AEC device, which enhances portability by transmitting X-ray image data and an X-ray sensing signal for AEC to an external device through wireless communication.

The above description is merely illustrative of the technical idea of the present disclosure, and various modifications and changes can be made thereto by those skilled in the art without departing from the essential characteristics of the present disclosure.

Therefore, the embodiments of the present disclosure are not intended to limit the technical spirit of the present disclosure but to describe the technical idea of the present disclosure, and the technical spirit of the present disclosure is not limited by these embodiments.

The scope of protection of the present disclosure should be interpreted by the appending claims, and all technical ideas within the scope of equivalents should be construed as falling within the scope of the present disclosure.

What is claimed is:

1. An X-ray detector integral with an automatic exposure control (AEC) device, the X-ray detector comprising:
   an X-ray detection part configured to detect X-rays irradiated from an X-ray source and generate X-ray image data; and
   an automatic exposure detection board located below the X-ray detection part and configured to generate an X-ray sensing signal for automatic exposure control based on residual X-rays which have passed by or through the X-ray detection part,
   wherein the X-ray detector further comprises:
   an electromagnetic wave absorption sheet configured to absorb energy from the X-rays for protecting components within the X-ray detector;
   a scattering prevention sheet configured to prevent back-scattering of the X-rays; and
   a driving circuit fixing plate configured to fix a driving circuit of at least one X-ray sensor and the automatic exposure detection board,
   wherein the electromagnetic wave absorption sheet, the scattering prevention sheet and the driving circuit fixing plate are disposed between the at least one X-ray sensor and the automatic exposure detection board.

2. The X-ray detector of claim 1, wherein the X-ray detection part comprises:
   a photoconductor configured to absorb the X-rays to generate an electron-hole pair; and
   a thin-film transistor (TFT) configured to detect a dose of the X-rays as an electrical signal based on the electron-hole pair.

3. The X-ray detector of claim 2, wherein the photoconductor comprises at least one of amorphous selenium, perovskite, Cadmium Telluride (CdTe) or cadmium zinc telluride (CdZnTe).

4. The X-ray detector of claim 1, wherein the X-ray detection part comprises:
   a first scintillator configured to convert the X-rays into visible rays; and
   a first photodiode configured to convert the visible rays into an electrical signal.

5. The X-ray detector of claim 4, wherein the first scintillator comprises at least one of gadolinium oxysulfide (GoS), cesium iodide (CsI) or perovskite.

6. The X-ray detector of claim 5, wherein the perovskite is a compound represented by Formula 1 below:

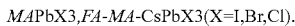

$MAPbX3, FA-MA-CsPbX3(X=I,Br,Cl)$.  Formula 1

7. The X-ray detector of claim 1, wherein the automatic exposure detection board comprises:
   a second scintillator configured to convert the residual X-rays into visible rays;
   a second photodiode configured to convert the visible rays into an electrical signal; and
   a thin-film transistor (TFT) configured to amplify the electrical signal and to output the amplified electrical signal.

8. The X-ray detector of claim 7, wherein the automatic exposure detection board comprises:
   a processor configured to obtain the amplified electrical signal as an X-ray sensing signal; and a transmitter configured to wirelessly transmit the X-ray sensing signal to a system controller or wirelessly transmit the X-ray sensing signal to a high-voltage generator.

9. The X-ray detector of claim 8, wherein the X-ray sensing signal includes information for determining whether the X-rays exceed a threshold dose of radiation for a patient.

10. The X-ray detector of claim 1, further comprising an upper frame disposed above the X-ray detection part,
    wherein the upper frame comprises:
    a decorative sheet including a pattern for adjusting a center for aiming the X-rays;
    a carbon fiber reinforced plastic (CFRP) plate; and
    a high-density polyethylene (HDPE) pad.

11. A device for facilitating automatic exposure control (AEC), the device comprising:
    at least one X-ray sensor configured to detect X-rays irradiated from an X-ray source for generating X-ray image data of a body part of a patient; and
    an automatic exposure detector configured to generate an X-ray sensing signal for automatic exposure control of the X-ray source based on residual X-rays from the X-rays which have passed by or through the at least one X-ray sensor,
    wherein the device further comprises:
    an electromagnetic wave absorption sheet configured to absorb energy from the X-rays for protecting components within the device;
    a scattering prevention sheet configured to prevent back-scattering of the X-rays; and
    a driving circuit fixing plate configured to fix a driving circuit of the at least one X-ray sensor and the automatic exposure detector,
    wherein the electromagnetic wave absorption sheet, the scattering prevention sheet and the driving circuit fixing plate are disposed between the at least one X-ray sensor and the automatic exposure detector.

12. The device of claim 11, further comprising a transmitter configured to wirelessly transmit the X-ray sensing signal for controlling the X-ray source,
    wherein the X-ray sensing signal includes information for determining whether the X-rays exceed a threshold dose of radiation for a patient.

13. A device for facilitating automatic exposure control (AEC), the device comprising:
    an upper frame having a pattern for adjusting a center for aiming X-rays, or being configured to support a body part of a patient;
    at least one X-ray sensor configured to detect X-rays irradiated from an X-ray source for generating X-ray image data of the body part of the patient;
    an automatic exposure detector part configured to generate an X-ray sensing signal for turning off the X-ray source based on residual X-rays remaining from the X-rays which have passed by or through the at least one X-ray sensor;
    an electromagnetic wave absorption sheet configured to absorb energy from the X-rays for protecting components within the device;
    a scattering prevention sheet configured to prevent back-scattering of the X-rays; and
    a driving circuit fixing plate configured to fix a driving circuit of the at least one X-ray sensor and the automatic exposure detector part,
    wherein the electromagnetic wave absorption sheet, the scattering prevention sheet and the driving circuit fixing plate are disposed between the at least one X-ray sensor and the automatic exposure detector part.

\* \* \* \* \*